United States Patent [19]

Scott et al.

[11] Patent Number: 4,738,956

[45] Date of Patent: Apr. 19, 1988

[54] HYDROCORTISONE COMPOSITION HAVING ENHANCED BIOAVAILABILITY AND PERCUTANEOUS ABSORPTION

[75] Inventors: Richard A. Scott, Burbank; Mitchell S. Wortzman, Los Angeles, both of Calif.; Eric Jungermann, Phoenix, Ariz.

[73] Assignee: Neutrogena Corporation, Los Angeles, Calif.

[21] Appl. No.: 941,699

[22] Filed: Dec. 15, 1986

Related U.S. Application Data

[63] Continuation-in-part of Ser. No. 577,513, Feb. 6, 1984, Pat. No. 4,678,663.

[51] Int. Cl.$^4$ .................. A61K 7/48; A61K 9/07; A61K 31/56
[52] U.S. Cl. .................. 514/179; 424/DIG. 5; 424/DIG. 10; 514/857; 514/859; 514/861; 514/862; 514/865; 514/889; 514/919; 514/969
[58] Field of Search .................. 514/179; 424/DIG. 5, 424/47, DIG. 10

[56] References Cited

U.S. PATENT DOCUMENTS 4,496 1/1985 Wong .................................. 514/179
4,233,295 11/1980 Hill et al. ........................... 514/179

Primary Examiner—Dale R. Ore
Attorney, Agent, or Firm—Richard R. Mybeck

[57] ABSTRACT

A new and improved topically applied pharmaceutical preparation for the treatment of itching, rash, eczema, insect bites, poison ivy and the like and an improved vehicle for delivering the active ingredients thereof to the human skin in a manner whereby the bioavailability and percutaneous absorption of the active ingredient is remarkably enhanced. The vehicle comprises a volatile silicone, a fatty alcohol having from 12-22 carbon atoms, hydrocortisone; and such preservatives or emulsifying agents as may be warranted.

9 Claims, No Drawings

HYDROCORTISONE COMPOSITION HAVING ENHANCED BIOAVAILABILITY AND PERCUTANEOUS ABSORPTION

INTRODUCTION

This invention relates to topical pharmaceutical preparations containing hydrocortisone as its essential active ingredient for the treatment of itching, rash, eczema, insect bites, poison ivy and the like and more particularly to a new and improved topically applied pharmaceutical product and means for delivering the same in a manner whereby the bioavailability and effectiveness of the active ingredient thereof is remarkably enhanced. This application is in part a continuation application from U.S. Ser. No. 577,513, filed Feb. 6, 1984, now U.S. Pat. No. 4,678,663.

BACKGROUND OF THE INVENTION

The prior art has traditionally delivered topically effective pharmaceutical agents in creams, lotions and gels, all of which require the user to soil his fingers and hands in the application of such medicaments and in the subsequent action of "rubbing it in". Further, such products are greasy, slow to dry and inevitably leave a residue which not only is visible, but rubs off onto clothing and the like, all of which are discomforting to the social ease of the user.

One variation from the traditional creams, lotions and gels occurred with the development of the so-called stick delivery systems which were used to apply antiperspirants, deodorants, lip balm, lip coloring and like ingredients which are generally applied to the surface of the skin.

Antiperspirant sticks based on the combination of a volatile silicone, a fatty alcohol and a powdered antiperspirant were recently developed and marketed. These sticks, however, have not been extended beyond simple antiperspirant sticks using water soluble inorganic antiperspirant salts. This limited use is the result of the known mechanism of antiperspirant vehicles and the need to intentionally design such delivery systems so as to limit the amount of active ingredient (antiperspirant) which can penetrate into the skin. For an antiperspirant to be efficacious, a large concentration of the active ingredient must be maintained on the surface of the skin from whence it is slowly dissolved and diffused into the apocrine ducts, rather than being absorbed through the skin. To extend this prior art to other pharmacologically active topical agents, it is necessary to greatly enhance the amount of the drug which is able to penetrate through the skin to reach the desired sites of action. This absorption of a drug through the skin is referred to as percutaneous absorption.

Nor does the typical lip balm formulation solve the problem because such products normally contain large amounts of wax (such as Beeswax, Carnauba, and the like), and oils, (such as, castor oil, lanolin and the like), whereupon a greasy/oily sensation is created on the skin which is not only unpleasant but gives the user the feeling of being "dirty". In addition, this type of formulation, as with antiperspirants, severely limits the percutaneous absorption of most drugs through the skin.

Likewise, the conventional creams and lotions fail to obviate the problems enumerated because the creams and lotions are excessively greasy and have the potential to sequester the active ingredient so that the percutaneous absorption of the drug and its efficacy is reduced.

SUMMARY OF INVENTION

An improved topically applied pharmaceutical preparation containing hydrocortisone as its principal active ingredient and including a novel delivery system by which the bioavailability and percutaneous absorption of the active pharmaceutical ingredient is remarkably enhanced, the "feel" of the product is pleasing to the user, it is simple and neat to use, and its compatibility enables hydrocortisone to be incorporated thereinto without any material depreciation of the unique properties accorded thereto.

Accordingly, one object of the present invention is to develop a consumer acceptable delivery system for applying an active pharmaceutical to the human skin which avoids the aforesaid disadvantages of the prior art creams, lotions, gels and sticks while enabling the user to readily control its application to a specified location with maximum effectiveness, a minimum of waste, and no mess.

Another object of the present invention is to provide a silky and non-greasy delivery system which is capable of spreading an active pharmaceutical ingredient evenly and smoothly on the skin and which leaves virtually no residue.

A further object of the present invention is to provide a new and improved delivery system which is compatible with dermatologically effective pharmaceuticals and is capable of delivering such pharmaceuticals with high efficiency and increased percutaneous absorption thereby increasing both the bioavailability of the active ingredient and its efficacy.

Still another object of the present invention is to provide an improved topically applicable pharmaceutical preparation which can be used to efficiently and efficaciously deliver hydrocortisone to the needed site.

These and still further objects as shall hereinafter appear are fulfilled by the present invention in a remarkably unexpected fashion as will be readily discerned from a careful consideration of the detailed description of certain exemplary embodiments thereof which hereafter appear.

DETAILED DESCRIPTION OF PREFERRED EMBODIMENTS

The present invention relates to a phrmaceutical preparation and more particularly to a semi-solid vehicle containing hydrocortisone for applying that to the human skin for the treatment of itching, rash, eczema, insect bites, poison ivy and the like. The special vehicle comprises a volatile silicone, such as dimethicone and cyclomethicone; a fatty alcohol having from 12 to 22 carbon molecules or a mixture of $C_{12}$ to $C_{22}$ fatty alcohols; hydrocortisone; and such preservatives, or emulsifying agents as may be warranted.

An important factor of the present invention is the use of a volatile silicone such as dimethicone, the cyclomethicones or equivalent cyclic silicones, which avoid the heavy oils and waxes heretofore employed and provide instead a silky and non-greasy lubricant which enables the active ingredient to be spread evenly and smoothly upon the skin. Once the active ingredient has been delivered to the selected site, the silicones will volatilize and leave no residue on the skin. Suitable silicones for use herein are available commercially from Dow Corning as 200 fluid (0.65cs), 344 fluid (formerly Q2-1053) and 345 fluid (formerly F1-3597).

The use of Dodecanol, Tridecanol, Tetradecanol, Pentadecanol, Hexadecanol (cetyl alcohol), Heptadecanol Octadecanol, Nonadecanol, Eicosanol, Heneiconsanol, and Docosanol (Stearyl alcohol) or mixtures thereof provide another important feature of the invention.

Specifically the basic delivery system of the present invention contains from about 20% up to about 40% weight percent (w/w) of fatty alcohol such as a mixture of stearyl and cetyl alcohol; from about 30% up to about 60% (w/w) volatile silicone such as dimethicone or a cyclomethicone; from about 0.1% up to about 10% (w/w) of the active drug; and from about 1% to about 10% (w/w) of various other ingredients such as preservatives, and/or emulsifying agents.

The system thus described has the further surprising advantage in that it is not limited just to water soluble ingredients but can also be employed in a most propitious manner with many insoluble ingredients when suspended in a fine particulate form (less than about 30 m) to form an acceptable product.

The specific details whereby our system is employed with hydrocortisone for the treatment of itching, rash, eczema, insect bites, poison ivy and the like shall now be described. Special attention is directed to the ability of this system to stabilize a number of drug ingredients which are known to be unstable in most common vehicles, and to accept those active ingredients which heretofore have not been acceptable in any effective vehicle systems.

Hydrocortisone when effectively incorporated into the present delivery system exhibits improved stability, and enhanced bioavailability as hereinafter demonstrated. The accepted use and the expected shelf-life, as determined by accelerated stability studies, for the hydrocortisone stick are reported in Table I along with a number of other active pharmaceutical agents which have been found useful when used therewith.

TABLE I

| INGREDIENT | USE | EXPECTED SHELF-LIFE* |
|---|---|---|
| Hydroquinone 2% | Skin Bleaching | 24–36 months |
| Benzoyl Peroxide 5% | Acne Treatment | 24 months |
| Coal Tar Extract 2% | Psoriasis Treatment | 36+ months |
| Allantoin .5% | Dry Skin Product | 24–36 months |
| Glycerin 5% | Dry Skin Product | 36+ months |
| Camomile Extract 1% | Anti-itch Product | 18 months |
| Butaben Picrate 1% | Burn Anesthetic | 18–24 months |
| Hydrocortisone .5% | General Steroid | 24–36 months |
| Providone-Iodine 1% | Antiseptic Product | 24–36 months |
| Bactimycin .5% | Antibiotic Product | 24–36 months |
| Diethyltoluamide 1% | Insect Repellent | 24–36 months |
| Papain | Psoriasis Treatment | 24–30 months |
| 13-Cis Retinoic Acid .1% | Acne Treatment | 18–24 months |

(*Note: When formulated in accordance with present invention.)

From Table I, it can be readily seen that the volatile silicone based vehicle system of the present invention provides an excellent matrix for the stabilization of hydrocortisone.

Hydrocortisone has already received FDA approval as a topical preparation for general steroid application and its efficacy therefor needs no further proof. Currently hydrocortisone topical preparations are available OTC at concentrations of up to 0.5% and by prescription at concentrations over 0.5%. According to published reports, the concentrations of 1% and 2.5% are the prescription strengths most typically designated by physicians.

The silicone/fatty alcohol ($C_{12}$–$C_{22}$) system of the present invention further offers a vehicle of low-irritancy potential. This is important in treating skin disorders or sensitive skin with any drug. Many of the vehicles currently used contain ethyl alcohol, isopropyl alcohol, glycols and other moderately irritating substances. The silicone/fatty alcohol system provides a non-stinging, non-irritating and low allergenic vehicle.

The increased bioavailability of the active pharmaceutical agent delivered in accordance with this disclosure, as compared to the more traditional vehicles such as creams and lotions, is a unique result. It is commonly known, in comparing the efficacies of different antiperspirant vehicles, such as creams, aerosols, roll-ons and sticks, that the determining factor is the level of the active ingredient (antiperspirant). That is, the same percentage of active antiperspirant ingredient will produce the same level of antiperspirant effect; regardless of the vehicle used.

As shown in Tables II-A, II-B and IIC, the present invention demonstrates a substantially improved drug bioavailability, and therefore efficacy, over the other commonly used vehicles containing the same percentage of hydrocortisone. In addition, the present invention demonstrates a substantially greater bioavailability than a commercial product containing over five times the active ingredient. (Compare Tables II-A, II-B and II-C, below.) These results are remarkable in comparison to what would be expected by simply utilizing the prior antiperspirant technology.

In one practice of the present invention using stearyl alcohol, all of the desired ingredients with the exception of the volatile silicone are mixed together and the mixture is then heated gently to about 80° C. until all of the ingredients are thoroughly mixed throughout the melted stearyl alcohol (MP=80° C.). The melted solution or suspension is then cooled to 60°–70° C. and the volatile silicone is added to the cooled mixture and stirred thereinto. When the silicone is thoroughly mixed throughout, the resulting mixture is poured into suitable molds or containers and allowed to cool until solidified. A propitious effect of this practice is that the active ingredient maintains its homogeneous dispersion throughout the solidified mass and there is little or no settling therein.

The invention has been successfully practiced to produce the stick compositions reported below which are then capable of delivering the noted active pharmaceutical ingredient to the desired sites in an easy and efficient manner.

The user employs the resulting stick by grasping the container in which the vehicle with its active ingredient has been disposed. The conventional push-up container, that is, a container having a base plate which is upwardly mobile in response to a force applied thereto by the consumer, which in turn forces the vehicle upwardly until an applicator surface is exposed above the upper rim of the container, can be considered to typify the container used herein. The user then manipulates the container in a stroke-wise fashion to paint the desired location with the mixture thereby delivering the active ingredient to the situs where its action is desired or required. This, of course is not intended to limit the use of the present invention to only stick forms, but is presented as an example of one potential use.

To further aid in the understanding of the present invention, and not by way of limitation, the following examples are presented.

EXAMPLE 1

A batch of hydrocortisone-containing vehicle is prepared to provide a product for the treatment of itching, rash, eczema, insect bites, poison ivy and the like. Note that such a product, to be effective, must be capable of penetrating the epidermis by the process of percutaneous penetration.

A mixture of hydrocortisone, PEG-1000, stearyl alcohol, cetyl alcohol, TEA-99%, and preservatives are stirred together and gently heated to 80° C. where it is maintained while all of the ingredients are thoroughly blended throughout the molten mass. The molten solution/suspension is then cooled to a temperature between 60°-70° C. and a volatile silicone (cyclomethicone) is added thereto and blended therein. After the silicone is thoroughly mixed with all of the other ingredients, the mixture is poured into a cylindrical mold or container and cooled further until it is completely solidified.

The resulting product, herein denominated "hydrocortisone stick" has the following analysis (in weight percent):

0.5% Hydrocortisone
21.0% Stearyl Alcohol
5.0% PEG-1000
5.0% Cetyl Alcohol
0.5% Preservatives
0.2% TEA-99%
67.8% Volatile Silicone

EXAMPLE 2

Sticks prepared according to the procedure of EXAMPLE I having 0.5%, 1.0%, and 2.5% (w/w) of hydrocortisone were tested for bioavailability against a major OTC product, namely, Cortaid ® 0.5% (Upjohn), and major Rx products at 1% and 2.5% (Hytone ®, Dermik) using the standard protocol for such tests based on FICK'S Law (see: Franz, T. J., "On the bioavailability of topical formulations . . . . " J. Amer. Academy of Dermatology, St. Louis, Vol 9, No 1, pp 63–73 at 68–69). The results are reported in Tables II-A, II-B and II-C, and expressed as penetration in micrograms over a period of 6 hours.

TABLE II-A

| Percutaneous Penetration of Hydrocortisone (in micrograms) | | |
|---|---|---|
| Time after Application hours | Example I (0.5% H) | Cortaid ® (0.5%) |
| 0.5 | 8.7 | 1.2 |
| 1.0 | 12.2 | 2.5 |
| 1.5 | 13.0 | 2.5 |
| 2.0 | 14.7 | 4.9 |
| 3.0 | 14.8 | 5.1 |
| 4.0 | 16.6 | 7.0 |
| 5.0 | 16.1 | 6.6 |
| 6.0 | 16.6 | 6.6 |

TABLE II-B

| Percutaneous Penetration of Hydrocortisone (in micrograms) | | |
|---|---|---|
| Time after Application hours | Example I (1.0% H) | Hytone (1.0%) |
| 0.5 | * | * |
| 1.0 | * | * |
| 1.5 | * | * |
| 2.0 | 9.2 | 16.5 |
| 3.0 | 16.4 | 16.7 |
| 4.0 | 16.0 | 16.7 |
| 5.0 | 19.4 | 17.8 |
| 6.0 | 19.6 | 17.9 |

*Data not available for 0.5 to 1.5 hours because buffer failure in one chamber.

TABLE II-C

| Percutaneous Penetration of Hydrocortisone (in micrograms) | | |
|---|---|---|
| Time after Application hours | Example I (2.5% H) | Hytone (2.5%) |
| 0.5 | 9.7 | 1.0 |
| 1.0 | 13.3 | 2.8 |
| 1.5 | 13.6 | 2.8 |
| 2.0 | 19.0 | 5.5 |
| 3.0 | 17.6 | 4.6 |
| 4.0 | 19.6 | 6.0 |
| 5.0 | 19.1 | 6.1 |
| 6.0 | 19.1 | 6.2 |

From the foregoing it becomes readily apparent that a novel and unique vehicle system has been herein described which delivers hydrocortisone in a form wherein the bioavailability and percutaneous absorption is remarkably enhanced and with which the physical disadvantages of prior art systems have been obviated. Of course, such modifications, alterations and adaptations as will readily occur to the skilled artisan confronted with this disclosure are intended within the spirit of the present invention which is limited only by the scope of the claims appended hereto.

Accordingly, what is claimed is:

1. A pharmaceutical preparation having enhanced bioavailability and percutaneous absorption comprising a mixture containing from about 20% up to about 40% (w/w) fatty alcohol having 12 to 22 carbon atoms or mixtures thereof; from about 30% up to about 60% (w/w) of a volatile silicone; from about 0.1% up to about 10% (w/w) of hydrocortisone; and from about 1% to about 10% (w/w) of an ingredient selected from the group consisting of a preservative, an emulsifier and a mixture thereof.

2. A preparation according to claim 1 in which said fatty alcohol comprises a mixture of stearyl and cetyl alcohol.

3. A preparation according to claim 1 in which said volatile silicone is cyclomethicone.

4. A preparation according to claim 1 in which said volatile silicone is dimethicone.

5. A preparation according to claim 3 in which said fatty alcohol comprises a mixture of stearyl and cetyl alcohol.

6. A preparation according to claim 4 in which said fatty alcohol comprises a mixture of stearyl and cetyl alcohol.

7. A pharmaceutical preparation for the treatment of itching, rash, eczema, insect bites, poison ivy and other skin disorders consisting of from about 0.1% up to about 10% (w/w) of hydrocortisone as its essential ingredient, said ingredient dispersed throughout a semi-solid vehicle having from about 20% up to about 40% (w/w) stearyl and cetyl alcohol; from about 30% up to about 60% (w/w) of a volatile silicone; and from about 1% to about 10% (w/w) of an ingredient selected from the group consisting of a preservative, an emulsifier and a mixture thereof.

8. A pharmaceutical preparation according to claim 7 in which said volatile silicone is cyclomethicone.

9. A pharmaceutical preparation according to claim 7 in which said volatile silicone is dimethicone.

* * * * *